United States Patent [19]

Hochstetler

[11] Patent Number: 4,549,029
[45] Date of Patent: Oct. 22, 1985

[54] SUBSTITUTED TETRAHYDROFURANS

[75] Inventor: Alan R. Hochstetler, Glen Rock, N.J.

[73] Assignee: Givaudan Corporation, Clifton, N.J.

[21] Appl. No.: 482,353

[22] Filed: Apr. 5, 1983

[51] Int. Cl.[4] ........................................... C07D 307/06
[52] U.S. Cl. ................................ 549/429; 252/522 R; 426/536; 568/813
[58] Field of Search ........................................ 549/429

[56] References Cited

U.S. PATENT DOCUMENTS

| 3,996,290 | 12/1976 | Tavares et al. | 568/425 |
|---|---|---|---|
| 4,067,906 | 1/1978 | Tavares et al. | 568/341 |
| 4,115,406 | 9/1978 | Vinals et al. | 549/356 |
| 4,198,323 | 4/1980 | Conrad et al. | 252/522 R |
| 4,404,127 | 9/1983 | van der Weerdt et al. | 252/522 R |

FOREIGN PATENT DOCUMENTS 0049543  4/1982  European Pat. Off. .

OTHER PUBLICATIONS

Chem. Abst. 61:3053C for N. I. Shuikin, Izv. Akad. Nauk SSSR, Ser. Khim. 1964, 746–747.
J. Ranfaing et al., Bull. de la Soc. Chim. de France 1974, 1048–1052.
E. Campaigne et al., J. Org. Chem. 32, (1967), 2372–2375.
G. M. Bennett et al., J. Chem. Soc. 1936, 1114–1120.
M. C. Kloetzel, J. Amer. Chem. Soc. 62, (1940), 3405–3410.

*Primary Examiner*—Richard L. Raymond
*Attorney, Agent, or Firm*—Robert F. Tavares

[57] ABSTRACT

Novel substituted tetrahydrofurans having a six-membered ring in the 4 position and methyl substituents in the 2 and 4 positions possess organoleptic properties described as fruity, citrus-like and reminiscent of grapefruit. These compounds are useful in fragrances and flavors.

2 Claims, No Drawings

SUBSTITUTED TETRAHYDROFURANS

THE INVENTION

The present invention provides novel odorant and flavorant compounds of the formula

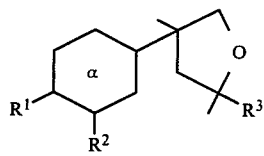

I wherein:

$R^1$, $R^2$ and $R^3$ represent hydrogen or methyl and may be alike or different except that $R^1$ and $R^2$ are not both methyl, and the six-membered ring designated by α can be a benzene ring, a cyclohexadiene ring, a cyclohexene ring or a cyclohexane ring.

The compounds of this invention are useful flavorants and odorants and are characterized by organoleptic properites which can be described as fruity, citrus-like and reminiscent of grapefruit.

The compounds of formula I can be prepared according to the following scheme.

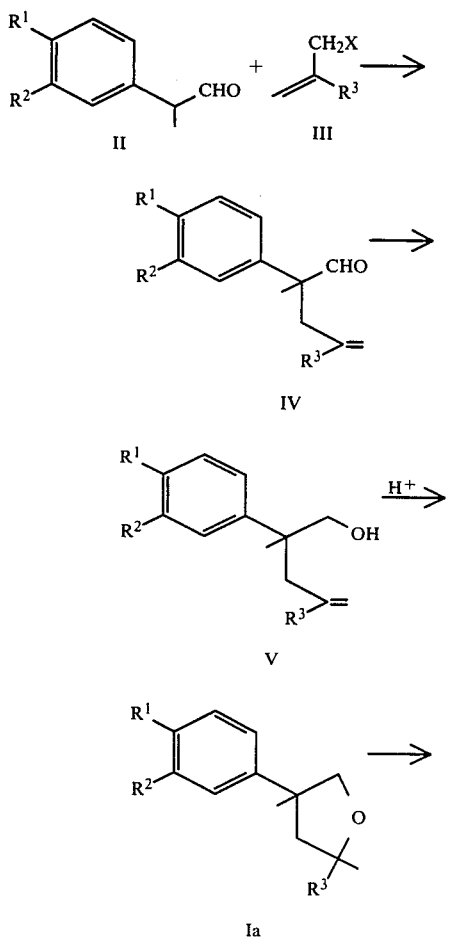

-continued

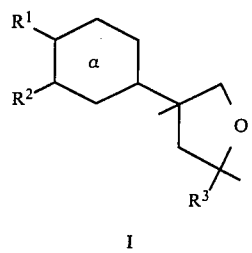

I

The starting aldehydes (II) are known or can be prepared from the corresponding acetophenone via a Darzen's reaction. The aldehyde II can then be alkylated with the appropriate allyl or methallyl halide (III) in a manner similar to that described in U.S. Pat. No. 3,996,290. (In structure III the group X can be chlorine, bromine or iodine, with chlorine preferred for economic reasons.)

The aldehydes IV can be converted into the novel alcohols V via a metal hydride reduction (e.g. LiAlH$_4$) or via a Meerwein-Ponndorf reduction. These alcohols are then converted to the novel tetrahydrofuran by an acid catalysed cyclization (e.g. H$_2$SO$_4$).

Conversion of the aromatic ring Ia to a cyclohexadiene can be accomplished via a dissolving metal (Birch) reduction. The 1,4-cyclohexadiene obtained can then be conjugated by treatment with base in a manner similar to that described in U.S. Pat. No. 4,067,906. This 1,3-cyclohexadiene can then be converted to a cyclohexene by methods similar to those known in the art, e.g. via a lithium in ammonia reduction. Either the cyclohexadiene ring or the cyclohexene ring can be converted to a cyclohexane ring via catalytic hydrogenation over a suitable catalyst (e.g. 5% Pd/C).

The compounds of formula I wherein the ring designated by α is a phenyl ring or a cyclohexyl ring have the further advantage of being extremely stable to chemical attack. This makes them particularly useful in functional products having active ingredients such as bleach and heavy duty cleaning products.

DESCRIPTION OF THE PREFERRED EMBODIMENTS

Formula I embraces a number of compounds which are useful in flavors and fragrances. They are characterized by the perfumer and flavorist as being clean, pleasant and natural, and as having fruity, floral and citrus notes and notes somewhat reminiscent of grapefruit. They are particularly suitable for adding these interesting notes to fragrance and flavor formulations and are suitable for adding freshness, intensity and character to the top notes.

While the compounds of formula I have basic characteristics in common, some are preferred over others. For fragrances, those compounds which have the formula Ib are preferred;

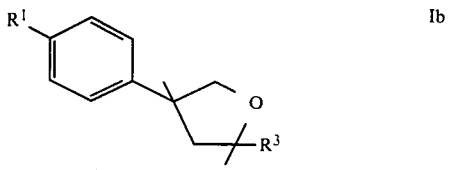

Ib the compounds wherein $R^3$ is methyl being especially preferred. The especially preferred species have a more desirable citrus-floral character than their analogs and contribute this quality to the top note which is highly desirable, especially in colognes (men's or women's), soaps and shampoos. The contribution such compounds make to the top note causes the fragrance to appear fresher and more desirable to the perfumer.

In applications where stability is important, e.g. in bleaches, detergents and heavy duty cleaning products, those compounds of formula I wherein the ring designated by α is a phenyl or cyclohexyl ring are preferred. Again those compounds of formula Ib where $R^3$ is methyl are especially preferred for the finer quality of their odors.

The compounds of formula I are compatible with a wide variety of other materials. They blend well with woody notes such as vetiver notes. They blend especially well with fruity and floral notes. They are particularly useful in a wide variety of fragrances, to provide lift and freshness to the top note. Of all the compounds of formula I, the 4-p-tolyl-2,2,4-trimethyltetrahydrofuran stands out as being the one most compatible with a number of fragrance types and as having more of the fresh, citrus, fruity-floral character with very little of the harsher nootkatone character.

The tetrahydrofurans of formula I may be mixed with other fragrance materials to provide perfume bases, said bases being suitable for use in finished products such as perfumes, toilet waters and functional products such as hand creams, cold creams, lotions, dipilatory creams, shampoos, soaps, detergents, room sprays and the like. The amount of the tetrahydrofuran used in such perfume bases will depend on the creativity and preference of the perfumer and could range from as low as 0.1% in some cases to as high as 90% in special cases. In most fragrance bases it is contemplated that ranges between 0.5% to 20% would be used.

The tetrahydrofurans of formula Ib have been found to be particularly suitable for masking, modifying or enhancing the odor of heavy duty cleaning products including bleach products. They have been tested and found to be stable in 5–6% aqueous sodium hypochlorite solution. Neither the oxidizing power of the solution nor the olfactive integrity of the odorant was deleteriously affected, even after standing several weeks at room temperature.

Those formula I chemicals which have a harsher nootkatone character appeal most to the flavorist. The compound Ib wherein both $R^1$ and $R^3$ are hydrogen is especially preferred.

In flavors, the compounds of formula I are again used to provide special contributions to the top note of the flavor to make it appear fresher, more intense and more citrus-like. This quality makes them particularly useful in fruit type flavors, especially the citrus flavors, e.g. orange, lemon, lime, grapefruit. They are also useful in the berry type flavors, e.g. blueberry, raspberry, strawberry, blackberry and the like.

The tetrahydrofurans of this invention can be added to foodstuffs, drinks and/or luxury consumables per se or they can be used to prepare flavoring compositions which can be added to them. A flavoring composition is comprised of a mixture of flavor imparting substances and perhaps a diluent, carrier and/or other adjuvants. These flavoring mixtures are then used to impart flavors to foodstuffs. Depending on the compound to be used, the flavor desired and the foodstuff to be flavored, the amount of the compound of formula I used in the flavor composition can vary over a wide range. The compounds of formula I may be as little as 0.001% of the flavor imparting substances present. In most applications, however, the compound would be a level of about 0.01% to 1.0% of the flavor imparting substances present. Levels as high as 10% may be desirable in some applications and, as has been mentioned above, the compound itself may be added to foodstuffs to improve, enhance and/or alter the flavor.

The flavoring substances described above are added to or incorporated into the foodstuffs to be flavored using methods well known in the art. The amount of flavoring composition used will depend on the flavor to be imparted and the foodstuff flavored. The compounds of formula I can be used in foodstuffs at levels as low as 0.01 parts per million to as much as 100 parts per million. In most foodstuffs, the level of compound used will be in the range of about 0.1 parts per million to about 10 parts per million.

Such foodstuffs are intended to include, but are not limited to chewing gums, candies, jellies, gelatins, desserts, liquors, yogurts, teas, and the like.

ILLUSTRATION OF THE PREFERRED EMBODIMENTS

The following examples are provided to illustrate further the practice of the present invention and should not be construed as limiting.

Infrared spectroscopy, mass spectroscopy, nuclear magnetic resonance spectroscopy and gas-liquid chromatography were used to analyze the products. Weights are given in grams.

EXAMPLE I

Preparation of 4-phenyl-2,2,4-trimethyltetrahydrofuran (a) A 376 g sample of 2,4-dimethyl-2-phenyl-4-pentenal (prepared via the method of U.S. Pat. No. 3,996,290) was added to 38 g of lithium aluminum hydride in 1200 ml of anhydrous ether over a 1 hr period with cooling to maintain 25° C. At the end of the addition, 76 g of water and 61 g of 10% aqueous sodium hydroxide were carefully added and the mixture was stirred for 2 hrs. The mixture was filtered, concentrated on a rotary evaporator and distilled, affording 370 g of 2,4-dimethyl-2-phenyl-4-penten-1-ol, (bp 125°–127°/0.5 mm Hg), in a 97% yield and a purity of 99%. Spectral data were in agreement with the assigned structure.

(b) A 312 g sample of the alcohol obtained in part (a) above was fed into a rapidly stirred 62% sulfuric acid solution at 30° C. over 0.5 hrs. The temperature was maintained at 30° C. with cooling as necessary for an additional 1.0 hr. The layers were then separated and the organic phase washed neutral with 10% sodium carbonate solution. Distillation afforded 243 g of 4-phenyl-2,2,4-trimethyltetrahydrofuran, (bp 80°–82° C./0.3 mm Hg), in a 77% yield and a purity of 99%. This material exhibited an intense citrus, grapefruit odor.

EXAMPLE II

Preparation of 2,4-dimethyl-4-phenyltetrahydrofuran (a) Following the procedure of part (a) of Example I a 400 g sample of 2-methyl-2-phenyl-4-pentenal was reduced with 30 g of lithium aluminum hydride in 1200 ml of anhydrous ether. Usual workup and distillation afforded 386 g (96% yield) of the desired 2-methyl-2- phenyl-4-penten-1-ol (bp 112°–114° C./0.5 mm Hg) with a purity of 97%.

(b) Following the procedure of part (b) of Example I a 220 g sample of the alcohol obtained in part (a) above was treated at 30° with 250 g of 85% sulfuric acid for 3 hrs. Usual workup and distillation gave 169 g (77% yield) of the desired 2,4-dimethyl-4-phenyltetrahydrofuran (bp 96°–97°/0.7 mm Hg) shown to be a 54:46 mixture of cis and trans isomers by capillary gas chromatography. This material possesses a grapefruit, citrus odor.

EXAMPLE III

Preparation of 4-(4-methylphenyl)-2,2,4-trimethyltetrahydrofuran and 4-(3-methylphenyl)-2,2,4-trimethyltetrahydrofuran (a) Following the procedure of part (a) of Example I a 353.5 g sample of 2,4-dimethyl-2-(4-methylphenyl)-4-pentenal was reduced with 30 g of lithium aluminum hydride in 1100 ml of anhydrous ether. Usual workup and distillation afforded 335 g (94% yield) of the desired 2,4-dimethyl-2-(4-methylphenyl)-4-penten-1-ol (bp 136°–138° C./0.7 mm Hg) with a purity of 95%.

(b) Following the procedure of part (b) of Example I a 260 g sample of the alcohol obtained in part (a) above was treated at 27° C. with 200 g of 62% sulfuric acid for 1 hr. Usual workup and distillation gave 221 g (85% yield) of the desired 4-(4-methylphenyl)-2,2,4-trimethyltetrahydrofuran (bp 110°–112° C./0.7 mm Hg) with a purity of 98%. This material possesses a fruity, grapefruit, floral odor.

(c) The 4-(3-methylphenyl)-2,2,4-trimethyltetrahydrofuran was also prepared (bp 70.5° C./0.6 mm Hg) with a purity of 98.1%. This material possesses a floral, bitter, fruity, citrus odor.

EXAMPLE IV

Preparation of 2,4-dimethyl-4-(4-methylphenyl)tetrahydrofuran (a) Following the procedure of part (a) of Example I a 356 g sample of 2-methyl-2-(4-methylphenyl)-4-pentenal was reduced with 30.4 g of lithium aluminum hydride in 1100 ml of anhydrous ether. Usual workup and distillation afforded 332 g (92% yield) of the desired 2-methyl-2-(4-methylphenyl-4-penten-1-ol (bp 128°–130° C./0.7 mm Hg) with a purity of 92%.

(b) Following the procedure of part (b) of Example I a 190 g sample of the alcohol obtained in part (a) above was treated at 30° C. with 400 g of 80% sulfuric acid for 1 hr. Usual workup and distillation gave 116 g (61% yield) of the desired 2,4-dimethyl-4-(4-methylphenyl)-tetrahydrofuran (bp 106°–108° C./0.5 mm Hg) with a purity of 92%, shown to be a 53:47 mixture of cis and trans isomers by capillary gas chromatography. This material possesses a citrus, fatty odor.

EXAMPLE V

Preparation of 4-(1,4-cyclohexadienyl)-2,2,4-trimethyltetrahydrofuran

A 150 g sample of 4-phenyl-2,2,4-trimethyltetrahydrofuran was added to 1000 ml of anhydrous ammonia, followed by 109 g of anhydrous ethanol. To this mixture was added portionwise over 1 hr 18.7 g of lithium wire. The mixture was allowed to stir at −33° C. for an additional 2 hrs., then sufficient ammonium chloride was added to discharge any residual blue color. The ammonia was allowed to evaporate and the residue was treated with 500 ml of hexane and 500 ml of water. The organic layer was separated and washed with 10% sulfuric acid solution until slightly acidic. The organic layer was washed with 10% soda ash solution and the solvent was removed on a rotary evaporator. Distillation afforded 128 g (84% yield) of the desired 4-(1,4-cyclohexadienyl)-2,2,4-trimethyltetrahydrofuran (bp 83°–84°/0.6 mm Hg) with a purity of 95%. Spectral data were in full agreement with the assigned structure. This material possesses a citrus, grapefruit, floral odor.

EXAMPLE VI

Preparation of 4-cyclohexyl-2,2,4-trimethyltetrahydrofuran

An 82 g sample of 4-(1,4-cyclohexadienyl-2,2,4-trimethyltetrahydrofuran was slurried with 3 g of 5% Pd/C catalyst. Intermediate heat evolution was noted and no hydrogen was absorbed upon attempted reduction in a Parr shaker at 50° C. and 50 psi. Vpc analysis after filtration from the catalyst showed a 44:56 ratio of two products resulting from disproportionation: the desired cyclohexyl compound and the phenyl compound. A 64 g sample of this mixture was treated with an additional 3 g of 5% Pd/C in a high pressure autoclave at 150° C. and 300 psi until hydrogen uptake ceased. The catalyst was filtered and the residue was distilled affording 58 g (89% yield) of the desired 4-cyclohexyl-2,2,4-trimethyltetrahydrofuran (bp 75°–76° C./0.5 mm Hg) with a purity of 99%. Spectral data were in agreement with the assigned structure. This material possesses a citrus, green, floral odor.

EXAMPLE VII

Use of the Novel Substituted Tetrahydrofurans As Odorants

A. Citrus Base

| Components | Parts by weight |
| --- | --- |
| Linalyl Acetate | 250 |
| Linalool | 250 |
| Terpinyl Acetate | 75 |
| d-Limonene | 350 |
| Lemarome ® (Givaudan) (Citral) | 25 |
| Dipropylene Glycol | 25 |
| | 975 |

The above base formulated without a compound of formula I has a citrus odor characteristic of orange and lemon.

The addition of 25 parts of a compound of formula I had a beneficial effect on the base. In each case the citrus character was improved. The compounds of formula Ib wherein $R^3$ is methyl provided a more desirable fruity-citrus-floral contribution than those compounds wherein $R^3$ is hydrogen. These latter compounds and those compounds of formula I wherein the ring designated by α is an unsubstituted cyclohexadienyl or cyclohexyl had a somewhat more tart-nootkatone contribution. The most desirable effect was provided by the 4-p-tolyl-2,2,4-trimethyltetrahydrofuran.

B. Cologne Base

| Components | Parts by weight |
| --- | --- |
| Anisic Aldehyde | 100 |
| Benzyl Acetate | 150 |
| Amyl Cinnamic Aldehyde | 100 |

-continued

| Components | Parts by weight |
| --- | --- |
| Jasverate ® (Givaudan) (Ethylidene norbornyl propionates and ethyl nortricyclyl propionates) | 50 |
| Linalool, Synthetic | 250 |
| Methyl Anthranilate | 100 |
| Petitgrain, South American | 190 |
| Yara-Yara | 50 |
| | 990 |

The addition of ten parts of a compound of formula I to the Cologne base contributed a beneficial citrus effect. Again, the compounds of formula Ib wherein $R^3$ was methyl contributed a smoother, milder citrus which was somewhat fruitier and more floral than the others. The other compounds of formula I contributed a somewhat more tart citrus effect. In all cases the top note was fresher and had better lift.

C. Chypre Base

| Components | Parts by weight |
| --- | --- |
| Labdanum Soluble Resin | 10 |
| Patchouli Oil | 75 |
| Vetiver Acetate | 50 |
| Geraniol | 50 |
| Phenyl Ethyl Alcohol | 25 |
| Ylang Oil Bourbon | 50 |
| Civet (2% in Ethanol) | 40 |
| Lavender Oil 38/42 (Givaudan Specialty Base) | 50 |
| Raldeine ®, Gamma (Methyl ionone) | 100 |
| Coumarin | 30 |
| Musk Ketone | 50 |
| Musk Ambrette | 25 |
| Oak Moss Soluble Resin | 60 |
| Bergamot, Synthetic | 355 |
| Estragole | 10 |
| | 980 |

The above Chypre base is described as fougere, sweet, powdery, animalic, woody. Compounds of formula I were added to the base in an amount of 20 parts by weight with noteworthy results. Both compounds of formula Ib wherein $R^3$ is methyl enhanced the floral-citrus note giving a bouquet effect. Additionally the compound wherein $R^1$ is methyl added a sweetness and fruitiness to the base.

Both compounds of formula Ib wherein $R^3$ is hydrogen added a green character. The compound wherein $R^1$ is also hydrogen contributed a strong citrus green character and that wherein $R^1$ is methyl added a fresh-floral-green quality, especially to the top note.

Other compounds of formula I were found to have analogous effects. For example, 4-(1,4-cyclohexadienyl)-2,2,4-trimethyltetrahydrofuran was found to add a green, citrus character, while 4-cyclohexyl-2,2,4-trimethyltetrahydrofuran was found to add a fresh, floral quality, especially to the topnote.

D. Muguet Base

| Components | Parts by weight |
| --- | --- |
| Citronellol, Synthetic | 100 |
| Phenyl Ethyl Alcohol | 150 |
| Benzyl Acetate | 150 |
| Hedione (IFF) (Methyl dihydrojasmonate) | 50 |
| Rosoxide [2-(2-Methyl-1-and 2-propenyl)-4-methyltetrahydropyrans] | 1 |
| Geranium Oil Bourbon | 10 |
| Hydroxycitronellal | 100 |

-continued

| Components | Parts by weight |
| --- | --- |
| Lyral (IFF) [3(and 4)-(4-Methyl-4-hydroxy-amyl)-Δ3-cyclohexenecarboxaldehyde] | 20 |
| | 20 |
| Terpineol Extra | 150 |
| Ylang, Synthetic | 30 |
| p-Cresyl Phenyl Acetate | 5 |
| Cyclamen Aldehyde | 15 |
| Heliotropine | 40 |
| gamma-Decalactone | 1 |
| Citronellyl Acetate | 5 |
| Viridine TM (Givaudan) (Phenyl acetaldehyde dimethylacetal) | 1 |
| Linalool | 40 |
| Cinnamyl Acetate | 15 |
| gamma-Undecalactone | 2 |
| p-Hydroxyphenylbutan-2-one (1% in Ethanol) | 1 |
| Methyl Anthranilate | 1 |
| Dipropylene Glycol | 3 |
| Phenyl Propyl Alcohol | 30 |
| | 920 |

Compounds of formula I added to the muguet base in an amount of 80 parts by weight generally enhanced the character of the floral blend, the particular effect being dependent on the compound used. Of the compounds of formula Ib wherein $R^3$ is methyl, that wherein $R^1$ is hydrogen imparted a fresh, citrus character while that wherein $R^1$ is methyl enhanced a general fruity character.

Of the formula Ib compounds wherein $R^3$ is hydrogen, that wherein $R^1$ is also hydrogen strengthened the floral odor adding a tart, green, citrus quality while that wherein $R^1$ is methyl added a woody character. Tart, bitter, citrus character was also added by 4-(1,4-cyclohexadienyl)-2,2,4-trimethyltetrahydrofuran. A mild citrus note was added by 4-cyclohexyl-2,2,4-trimethyltetrahydrofuran.

E. Soap Fragrance (Oriental)

Addition of about 3% of a compound of formula Ib wherein $R^3$ is methyl to a soap fragrance of the oriental type made the fragrance fresher and added intensity and character to the top note.

F. Shampoo Fragrance (Floral)

Addition of 10% of a compound of formula Ib wherein $R^3$ is methyl to a fragrance base used in a shampoo added an interesting freshness to the top note.

EXAMPLE VIII

Use of Novel Substituted Tetrahydrofurans As Flavorants

A. Grapefruit flavor

A standard test solution was prepared containing 10 ppm of grapefruit oil in a ten percent sugar solution.

The presence of 2,4-dimethyl-4-phenyltetrahydrofuran in the standard test solution at a level of 2 ppm made a beneficial contribution. All four flavorists on the test panel preferred the drink having the added compound stating that it tasted more like natural grapefruit juice than the solution without the added compound.

The compound 4-(1,4-cyclohexadien-1-yl)-2,2,4-trimethyltetrahydrofuran was tested in the same way with the same results.

The compound 4-phenyl-2,2,4-trimethyltetrahydrofuran altered the drink in a slightly different way. This compound, at a level of 2 ppm, made the drink more berry-like and more citrus-like in character.

B. Blueberry Flavor

| Components | Parts by weight |
| --- | --- |
| Ethyl Acetate | 50 |
| cis-3-Hexenol | 10 |
| Amyl Butyrate | 5 |
| Ethyl Isovalerate | 20 |
| Linalool | 10 |
| Vanillin | 5 |
| | 100 |

A blueberry flavor was made by adding 1.0 g of the above mixture to 99 g of 95% ethanol. A standard blueberry flavored drink was prepared by adding 2.0 g of the blueberry flavor, 100 g sucrose and 0.5 g malic acid to 899.3 g water. To 100 g of the standard drink was added 0.02 g of a 0.1% solution of 4-phenyl-2,2,4-trimethyltetrahydrofuran in 95% ethanol (0.2 ppm).

A comparison of the treated and untreated blueberry flavored drinks was made by a test panel of four flavorists. All preferred the treated drink stating that it was rounder, had enhanced aroma and a more natural blueberry flavor.

I claim:

1. A compound of the formula

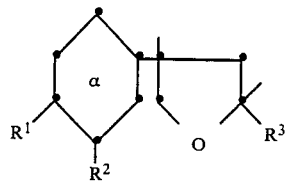

I wherein:

$R^1$, $R^2$ and $R^3$ represent hydrogen or methyl and may be alike or different except that $R^1$ and $R^2$ are different, and the six-membered ring designated by $\alpha$ is a benzene ring, a cyclohexadiene ring, a cyclohexene ring or a cyclohexane ring.

2. A compound of claim 1 wherein $R^1$ and $R^3$ are both methyl.

* * * * *